US 11,141,092 B2

(12) United States Patent
Stephens et al.

(10) Patent No.: US 11,141,092 B2
(45) Date of Patent: Oct. 12, 2021

(54) METHOD AND SYSTEM FOR INCORPORATING PHYSIOLOGICAL SELF-REGULATION CHALLENGE INTO GEOSPATIAL SCENARIO GAMES AND/OR SIMULATIONS

(71) Applicant: U.S.A. AS REPRESENTED BY THE ADMINISTRATOR OF NASA, Washington, DC (US)

(72) Inventors: Chad L. Stephens, Poquoson, VA (US); Alan T. Pope, Poquoson, VA (US); William Hollingsworth, Farmville, VA (US)

(73) Assignee: UNITED STATES OF AMERICA AS REPRESENTED BY THE ADMINISTRATOR OF NASA, Washington, DC (US)

( * ) Notice: Subject to any disclaimer, the term of this patent is extended or adjusted under 35 U.S.C. 154(b) by 407 days.

(21) Appl. No.: 15/787,105

(22) Filed: Oct. 18, 2017

(65) Prior Publication Data
US 2018/0103867 A1    Apr. 19, 2018

Related U.S. Application Data

(60) Provisional application No. 62/410,081, filed on Oct. 19, 2016.

(51) Int. Cl.
*G09B 19/00* (2006.01)
*A63B 24/00* (2006.01)
(Continued)

(52) U.S. Cl.
CPC ............ *A61B 5/375* (2021.01); *A61B 5/0205* (2013.01); *A61B 5/486* (2013.01); *A61B 5/742* (2013.01);
(Continued)

(58) Field of Classification Search
CPC .................................................. A63B 24/0059
See application file for complete search history.

(56) References Cited

U.S. PATENT DOCUMENTS 4,337,049 A    6/1982 Connelly
4,508,510 A    4/1985 Clifford
(Continued)

OTHER PUBLICATIONS

F. Buttussi, et al. Bringing mobile guides and fitness activities together: a solution based on an embodied virtual trainer. 2006. [ retrieved from internet on Jun. 2, 2021] <URL: https://dl.acm.org/doi/10.1145/1152215.1152222> (Year: 2006).*

(Continued)

*Primary Examiner* — Bion A Shelden
(74) *Attorney, Agent, or Firm* — Shawn P. Gorman; Jonathan B. Soike; Helen M. Galus

(57) ABSTRACT

A method of providing physiological self-regulation challenges prior to participating in a series of activities or exercises at a series of predefined locations includes determining a physiological goal associated with each location. A sensing device measures a physiological state of a user, and a mobile communication device communicates to a user whether or not the user has achieved the physiological goal for the challenge. The level of difficulty of the physiological goal may be reduced if the user does not meet the goal. The physiological goal may comprise a brain state that is conducive to learning, and the sensing device may be configured to measure brain state values representing cognitive engagement. Upon achievement of each physiological goal, the participant is provided with a reward such as information concerning the current predefined location and/or information concerning the next predefined location.

16 Claims, 9 Drawing Sheets

(51) Int. Cl.

| | | |
|---|---|---|
| *G09B 5/12* | (2006.01) | |
| *A61B 5/375* | (2021.01) | |
| *A63F 13/216* | (2014.01) | |
| *G09B 5/02* | (2006.01) | |
| *A63G 31/00* | (2006.01) | |
| *A61B 5/00* | (2006.01) | |
| *A61B 5/0205* | (2006.01) | |
| *A63F 13/85* | (2014.01) | |
| *A63G 33/00* | (2006.01) | |
| *A63F 13/212* | (2014.01) | |
| *A61B 5/024* | (2006.01) | |
| *A61B 5/1171* | (2016.01) | |
| *A63B 22/06* | (2006.01) | |
| *A63F 13/67* | (2014.01) | |

(52) U.S. Cl.
CPC ........ *A63B 24/0062* (2013.01); *A63F 13/212* (2014.09); *A63F 13/216* (2014.09); *A63F 13/85* (2014.09); *A63G 31/00* (2013.01); *A63G 33/00* (2013.01); *G09B 5/02* (2013.01); *G09B 5/125* (2013.01); *G09B 19/00* (2013.01); *G09B 19/0061* (2013.01); *A61B 5/02438* (2013.01); *A61B 5/1176* (2013.01); *A61B 5/6898* (2013.01); *A63B 22/0605* (2013.01); *A63F 13/67* (2014.09)

(56) References Cited

U.S. PATENT DOCUMENTS

| | | | |
|---|---|---|---|
| 5,377,100 | A | 12/1994 | Pope et al. |
| 5,626,140 | A | 5/1997 | Feldman et al. |
| 5,697,791 | A | 12/1997 | Nashner et al. |
| 5,702,323 | A | 12/1997 | Poulton |
| 5,743,744 | A | 4/1998 | Cassily et al. |
| 5,907,819 | A | 5/1999 | Johnson |
| 5,947,868 | A | 9/1999 | Dugan |
| 5,984,684 | A | 11/1999 | Brostedt et al. |
| 6,067,468 | A | 5/2000 | Korenman et al. |
| 6,093,146 | A | 7/2000 | Filangeri |
| 6,104,948 | A | 8/2000 | Bogart et al. |
| 6,126,449 | A | 10/2000 | Burns |
| 6,132,337 | A | 10/2000 | Krupka et al. |
| 6,148,280 | A | 11/2000 | Kramer |
| 6,212,427 | B1 | 4/2001 | Hoover |
| 6,259,889 | B1 | 7/2001 | LaDue |
| 6,261,189 | B1 | 7/2001 | Saville et al. |
| 6,277,030 | B1 | 8/2001 | Baynton et al. |
| 6,425,764 | B1 | 7/2002 | Lamson |
| 6,450,820 | B1 | 9/2002 | Palsson et al. |
| 6,463,385 | B1 | 10/2002 | Fry |
| 6,478,735 | B1 | 11/2002 | Pope et al. |
| 6,491,647 | B1 | 12/2002 | Bridger et al. |
| 6,527,700 | B1 | 3/2003 | Manico et al. |
| 6,682,351 | B1 | 1/2004 | Abraham-Fuchs et al. |
| 6,774,885 | B1 | 8/2004 | Oshri |
| 6,778,866 | B1 | 8/2004 | Bettwy |
| 6,786,730 | B2 | 9/2004 | Bleckley et al. |
| 8,062,129 | B2 | 11/2011 | Pope et al. |
| 8,164,485 | B2 | 4/2012 | Prinzel, III et al. |
| 8,628,333 | B2 | 1/2014 | Prinzel, III et al. |
| 8,827,717 | B2 | 9/2014 | Pope et al. |
| 8,858,323 | B2 | 10/2014 | Pope et al. |
| 8,858,325 | B2 | 10/2014 | Pope et al. |
| 9,084,933 | B1 | 7/2015 | Pope et al. |
| 9,283,468 | B2 | 3/2016 | Prinzel, III et al. |
| 9,848,812 | B1 | 12/2017 | Harrivel et al. |
| 2003/0013071 | A1 | 1/2003 | Thomas |
| 2003/0013072 | A1 | 1/2003 | Thomas |
| 2003/0087220 | A1 | 5/2003 | Bessette |
| 2005/0014113 | A1 | 1/2005 | Fleck et al. |
| 2005/0212212 | A1* | 9/2005 | Goodwin .................. A63F 1/00 273/292 |
| 2006/0061598 | A1* | 3/2006 | Mino ................ G06K 9/00228 345/629 |
| 2006/0136266 | A1* | 6/2006 | Tarassenko ............ G06Q 50/24 705/3 |
| 2008/0081692 | A1 | 4/2008 | Pope et al. |
| 2008/0275358 | A1* | 11/2008 | Freer ..................... G09B 19/00 600/544 |
| 2011/0009193 | A1* | 1/2011 | Bond ..................... A63F 13/212 463/36 |
| 2012/0315992 | A1* | 12/2012 | Gerson ................ H04W 4/029 463/42 |
| 2013/0006737 | A1* | 1/2013 | Goldberg ............. G06Q 30/02 705/14.12 |
| 2014/0030684 | A1* | 1/2014 | Steinmetz ............. A61B 5/486 434/247 |
| 2014/0256431 | A1* | 9/2014 | Pope ..................... A63F 13/211 463/31 |
| 2014/0316230 | A1* | 10/2014 | Denison ................. A61B 5/165 600/383 |
| 2014/0316869 | A1* | 10/2014 | ONeill .............. G06Q 30/0209 705/14.12 |
| 2014/0336473 | A1* | 11/2014 | Greco .................... A61B 5/486 600/301 |
| 2015/0081062 | A1* | 3/2015 | Fyfe ........................ A61B 5/486 700/91 |
| 2015/0088624 | A1* | 3/2015 | Frederick ........... G06Q 30/0209 705/14.12 |
| 2015/0092972 | A1* | 4/2015 | Lai ....................... H04R 1/1008 381/333 |
| 2015/0336010 | A1* | 11/2015 | Wiederkehr ............ A63F 13/85 463/42 |
| 2016/0077547 | A1* | 3/2016 | Aimone ............... A61B 5/0006 345/8 |
| 2016/0096075 | A1* | 4/2016 | Leppanen .......... A63B 24/0075 434/247 |
| 2016/0151674 | A1* | 6/2016 | Rauhala ................ G16H 20/40 434/247 |
| 2016/0240098 | A1* | 8/2016 | Shin ........................ G06F 3/015 |
| 2017/0193544 | A1* | 7/2017 | Glasgow ............ G06Q 30/0242 |
| 2017/0229037 | A1* | 8/2017 | Gazzaley ............. G09B 19/003 |
| 2017/0340920 | A1* | 11/2017 | Posio ...................... A61B 5/01 |
| 2018/0176736 | A1* | 6/2018 | Hong ..................... G06Q 50/22 |
| 2018/0286272 | A1* | 10/2018 | Mcdermott ........... A61B 5/744 |

OTHER PUBLICATIONS

Pope, A. T. et al., "Biocybernetic System Validates Index of Operator Engagement in Automated Task," Biological Psychology, May 1995, pp. 187-195, vol. 40, Issues 1-2.

Azcarate, A. et al., "Automatic Facial Emotion Recognition," Universiteit van Amsterdam, 1995, Vision and Image Understanding, pp. 38-59, vol. 61, No. 1.

Dinges, D. F. et al., "Optical Computer Recognition of Facial Expressions Associated with Stress Induced by Performace Demands," Aviation, Space, and Environmental Medicine, 2005, pp. B172-B182, vol. 76, No. 6, Section II.

Keltner D. et al., "Facial Expressions of Emotion," Handbook of Emotions, 2nd ed., 2000, pp. 236-245, Guilford Publications, Inc, New York.

Lerner, J. S. et al., "Facial Expressions of Emotion Reveal Neuroendocrine and Cardiovascular Stress Responses," Biological Psychiatry, 2007, pp. 253-260, vol. 61, No. 2.

Ratliff, M. S. et al., "Emotion Recognition Using Facial Expressions with Active Appearance Models," Third IASTED International Conference on Human Computer Interaction, Understanding Users, 2008, pp. 138-143.

Arkadiusz, Stopczynski et al., "Smartphones as Pocketable Labs: Visions for Mobile Brain Imaging and Neurofeedback," International Journal of Psychophysiology, 2014, vol. 91, pp. 54-66.

Maarten De Vos et al., "Towards a truly mobile aduitory brain-computer interface: Exploring the P300 to take away," International Journal of Psychophysiology, 2014, vol. 91, pp. 46-53, University of Oldenburg, Germany.

(56) References Cited

OTHER PUBLICATIONS

Stephens, C.L. et al., "Adaptive Automation for Mitigation of Hazardous States of Awareness," 2012, The Handbook of Operator Fatigue, Chapter 26, edited by Matthews, Desmond, Neubauer and Hancock.

Pope, Alan T. et al., "Biocybernetic Adaptation as Biofeedback Training Method," Springer, 2014, pp. 91-114.

Pope, A.T. et al., "Interpersonal Biocybernetics: Connecting through Social Psychophysiology," 2012, ACM International Conference on Multimodal Interaction, pp. 1-5, Santa Monica, CA.

Pope, A.T. et al., "Movemental: Integrating Movement and the Mental Game," Brain and Body Interfaces: Designing for Meaningful Interaction, May 7-12, 2011, pp. 1-5, Vancouver, BC Canada.

Harrivel, A. R. et al., "Psychophysiological Sensing and State Classification for Attention Management in Commercial Aviation", AIAA SciTech Forum, Jan. 4-8, (AIAA 2016-1490), San Diego, California.

Santiago-Espada, Y, et al., "The Multi-Attribute Task Battery II (MATB-II) Software for Human Performance and Workload Research: A User's Guide", Jul. 2011, NASA TM-2011-217164, pp. 1-74.

Hart, S. G., et al., Development of NASA-TLX (Task Load Index): Results of Empirical and Theoretical Research., Advances in Psychology, Human Mental Workload, 1988, pp. 139-183, vol. 52.

Fairclough, S.H., et al., Construction of the Biocybernetic Loop: A Case Study, Paper Presented at the 14th ACM International Conference on Multimodal Interaction, Oct. 22-26, 2012, pp. 1-8, Santa Monica, CA.

Wilhelm, F. H., et al., "Emotions Beyond the laboratory: Theoretical Fundaments, Study Design, and Analytic Strategies for advanced Ambulatory Assessment", Biological Psycology, Feb. 2010, pp. 552-569, vol. 84.

Stevens, R.H., et al., EEG-Related Changes in Cognitive-Workload, Engagement and Distraction as Students Acquire Problem Solving Skills, 11th International Conference, UM 2007, Jun. 25-29, pp. 187-196, Corfu, Greece.

Solovey, T.S., et al., Designing Implicit Interfaces for Physiology Computing: Guidelines and Lessons Learned Using fNIRS, ACM Transactions on Computer-Human Interaction, Jan. 2015, Article 35, pp. 35:1-35:27, vol. 6.

Harrivel et al., "Crew State Monitoring (CSM) and Trust in Humans (TIH)", NASA Langley Research Center Presentation Slides, Crew System and Aviation Operations Peer Review, Jan. 27, 2016, pp. 1-63, Hampton, Va.

Taylor, R.M., "Situational Awareness Rating Technique (SART): The development of a tool for aircrew systems design, Situational Awareness in Aerospace Operations", AGARD—Conference Proceeding-478, 1990, pp. 3-1-3-37, Neuilly Sur Seine, France.

Wilson, G.F., et al. "Real-Time Assessment of Mental Workload Using Psychophysiological Measures and Artificial Neural Networks," The Journal of Human Human Factors, Winter 2003, pp. 635-643, vol. 45, No. 4.

Wilson, G.F., et al., "Operator Functional State Classifications Using Multiple Psychophysiologcial Features in an Air Traffic Control Task", The Journal of Human Human Factors, Fall 2003, pp. 635-643, vol. 45, No. 3.

Li, F., "Improving Engagement Assessment by Model Individualization and Deep Learning", A Disseration Submitted to the Faculty of Old Dominion, Doctor of Philosophy, Electrical and Computer Engineering, Mar. 2015, Chapters 3 pp. 21-33 and Chapter 5 pp. 49-63.

Thomas, L. C., et al., Fatigue Detection in Commercial Flight Operations: Results Using Physiological Measures, Procedia Manufacturing, 2013, pp. 2357-2364, vol. 3.

\* cited by examiner

METHOD AND SYSTEM FOR INCORPORATING PHYSIOLOGICAL SELF-REGULATION CHALLENGE INTO GEOSPATIAL SCENARIO GAMES AND/OR SIMULATIONS

CROSS-REFERENCE TO RELATED PATENT APPLICATION

This patent application claims the benefit of and priority to U.S. Provisional Application No. 62/410,081, filed on Oct. 19, 2016, entitled "METHOD AND SYSTEM FOR INCORPORATING PHYSIOLOGICAL SELF-REGULATION CHALLENGE INTO PARCORSE/ORIENTEERING TYPE GAMES AND SIMULATIONS," the contents of which are hereby incorporated by reference in their entirety.

STATEMENT REGARDING FEDERALLY SPONSORED RESEARCH OR DEVELOPMENT

The disclosure described herein was made in the performance of work under a NASA contract and by employees of the United States Government and is subject to the provisions of Public Law 96-517 (35 U.S.C. § 202) and may be manufactured and used by or for the Government for governmental purposes without the payment of any royalties thereon or therefore. In accordance with 35 U.S.C. § 202, the contractor elected not to retain title.

OVERVIEW

Various devices for monitoring physiological signals have been developed. Current mobile/wearable personal technology enables the monitoring of a user's physiological signals (e.g., heartrate) and geographical location. Wearable technology may also be configured to communicate physiological information between users within a network.

Physiologically modulated videogames have been developed. Such games provide increased entertainment value by adding the challenge of requiring a player to master physiological self-regulation skill in addition to the hand-eye coordination required for conventional videogame play. Thus, controlling the physiological state and/or learning to self-induce physiologic changes is an additional skill requirement or challenge that may be added to videogames.

In addition to enhancing entertainment value by making games more exciting, physiologically modulated videogames also have advantages for encouraging health-enhancing physiological self-regulation skills or for therapeutic amplification of healthful physiological characteristics. Biofeedback, an effective treatment for various physiological problems, can be used to optimize physiological functioning in many ways. The benefits of biofeedback are typically only attained through a number of training sessions. Regular practice is typically required to maintain any gains achieved. Failure to adhere to regular training, especially at home, has been a problem known in biofeedback treatment regimes.

Various ways to provide bio-feedback in connection with videogames have been developed. Examples include U.S. Pat. Nos. 5,377,100, 6,450,820, 8,062,129, 8,827,717, and 8,858,325, which are hereby incorporated by reference in their entirety.

SUMMARY

One aspect of the present disclosure is a method of providing physiological self-regulation challenges to one or more users/participants during a series of predefined activities. The user completes a series of predefined tasks or activities. The tasks/activities may be performed at a series of spaced apart predefined locations. The predefined locations may be initially unknown to the user/participant, and the user/participant may be required to obtain information at each location that can be used to locate/find/identify the next location in the series. Alternatively, the locations may be provided to the user/participant at the start of the process.

The method includes determining, at (for) each location, a respective physiological goal, i.e., a requirement of a physiological self-regulation challenge. Different embodiments may determine the physiological goals using various techniques. In some implementations, a physiological goal for a location and/or activity at a location may be determined by retrieving the information from a database stored in a local or remote data storage. Additionally or alternatively, the determination of physiological goals may be based on user information or previous user performance (e.g., a user experience level or difficulty setting). For example, the database may list one or more physiological goals for different locations, task/activities, difficulties, performance levels, etc.

The physiological goal is typically related to the task/activity at each location. A sensing device measures a physiological state of a user and provides feedback to the user concerning the user's physiological state. For each challenge at each predefined location, a mobile communication device may communicate to a user whether or not the user has achieved the physiological goal for the challenge. For example, the level of difficulty of the physiological goal may be reduced if a user does not achieve an initial physiological goal for a challenge. The level of difficulty of the physiological goal may be reduced if the user has attempted to achieve the physiological goal for a challenge at least a threshold number of times. The method may include prompting a user to repeat a challenge if the user does not achieve the physiological goal for a challenge.

If the user achieves the physiological goal, the user is provided with a reward (e.g. information concerning the task/activity or other information such as information concerning the identity/location of the next predefined location.)

Different embodiments may present various different rewards to users in response to achieving the physiological goal(s). In some embodiments, one or more rewards may comprise information concerning the activity/task at the predefined location at which the user is located. For instance, if the predefined locations comprise exhibits/displays at a museum, the activities/tasks may comprise learning about the subject matter of each exhibit/display. In this example, a smartphone or other suitable device may be utilized to provide the user/participant with information concerning each exhibit/display, but only after the user achieves the physiological goal associated with each predefined location. Additionally or alternatively, if the predefined locations and activities comprise a series of exercise devices/stations, the reward may comprise activation of an exercise device and/or information concerning an exercise activity/task that must be completed before moving to the next predefined location (exercise device). Feedback concerning the user's physiological state may be provided before, during, or after the user participates in the activity/task at each predefined location. In some instances, the physiological goal may need to be achieved before the user initiates an activity/task. In some other instances, the physiological goal may need to be achieved while the user is doing the activity/task at each predefined location or may need to be achieved both before and during the activity/task. The physiological goal may comprise a brain state that is conducive to learning, and the sensing device may be configured to measure brain state values representing cognitive engagement. The activity may include a single user/participant, or it may include a plurality of groups of users/participants.

These and other features, advantages, and objects of the present disclosure will be further understood and appreciated by those skilled in the art by reference to the following specification, claims, and appended drawings.

DETAILED DESCRIPTION OF THE DISCLOSURE

Figure 1:
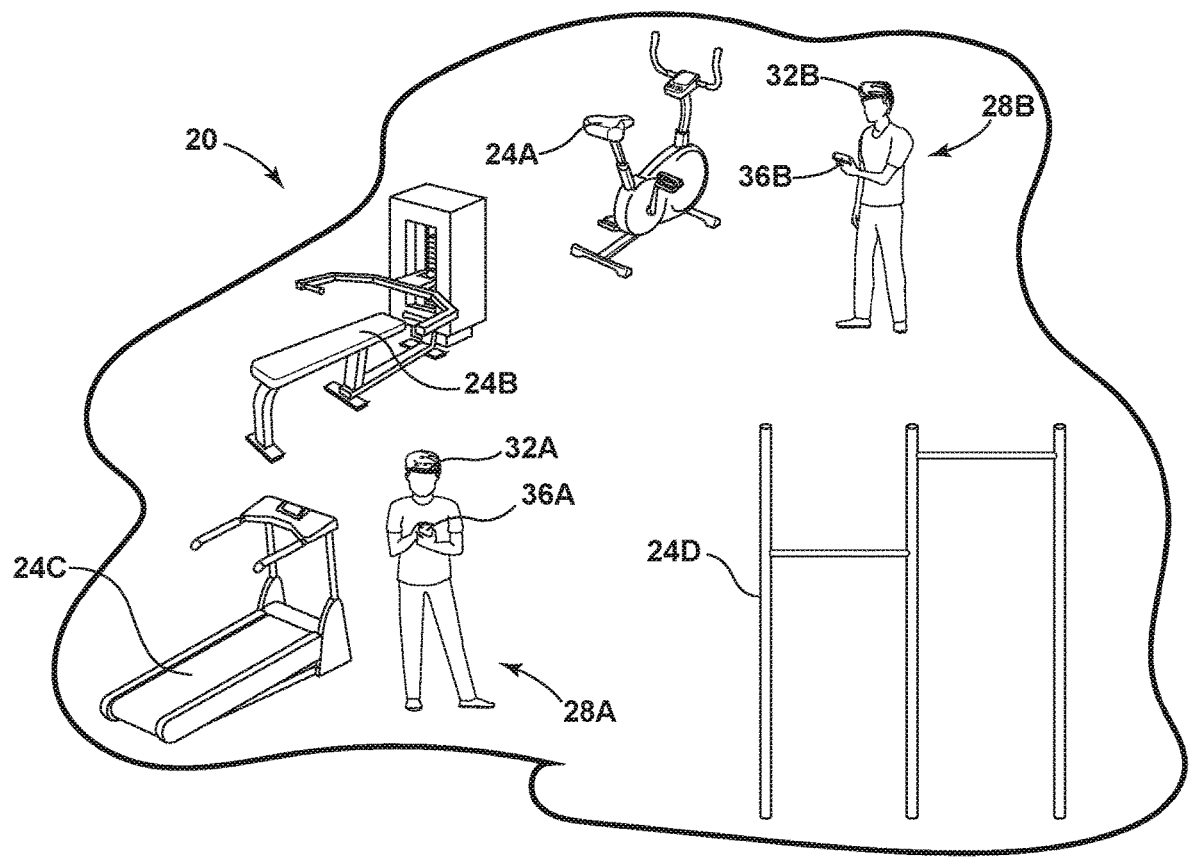
FIG. 1 is a partially schematic perspective view illustrating one aspect of the present disclosure.

For purposes of description herein, the terms "upper," "lower," "right," "left," "rear," "front," "vertical," "horizontal," and derivatives thereof shall relate to the disclosure as oriented in FIG. 1. However, it is to be understood that the disclosure may assume various alternative orientations and step sequences, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The present disclosure generally relates to integration of physiological measurement/self-regulation into various user activities, including but not limited to, orienteering, use of fitness trails and parcourses, rogaining, escape rooms, and/or tours. Users/participants perform a series of activities/tasks at a series of stations/locations. Self-regulation goals/challenges are provided for each station/location, and a portable communication device such as a smartphone may be used to provide users/participants with specific information if the user/participant achieves a predefined physiological self-regulation goal associated with each station/location.

Fitness trails such as running trails, bike trails, etc. can include/outdoor exercise equipment interspersed along the trail or course. Fitness trails that include outdoor exercise equipment may be commonly referred to as a "parcourse." Parcourses typically include a path or course equipped with obstacles or stations distributed along its length for exercising the human body to promote good health.

Orienteering is a type of activity that requires users to navigate from point to point in diverse and typically unfamiliar terrain using a map and compass. Participants may be incentivized to minimize the time required to complete one or more tasks.

Rogaining is somewhat similar to orienteering, but typically involves a team rather than an individual.

One or more embodiments integrate physiological self-regulation into parcourse/orienteering-type games and simulations to increase the user's motivation to engage in regular self-regulation practice to learn health-enhancing physiological self-regulation skills. Integrating physiological self-regulation into parcourse/orienteering-type games and simulations also increases engagement with the task of learning various topics and/or subject matter. One or more embodiments provide a new type of real-world game or simulation that combines elements of orienteering, parcourse training, rogaining, adventure fantasy, live action role playing, augmented-reality, massively multiplayer online location-based games, geocaching, treasure-hunting, and way-marking with a physiological self-regulation skill challenge.

The present disclosure describes methods and systems for delivering learning experiences through video games or simulations. Participants are presented with game and/or simulation challenges that build success within the games or simulations. The success built within the games or simulations is based upon physiological self-regulation training, which in turn may be built upon hardware and software construction tasks.

One or more embodiments may be utilized to educate the user on various topics and/or subject matter by blending, for example, parcourse/orienteering-type games and simulations with physiological self-regulation challenges. The physiological self-regulation challenges are designed to promote cognitive states that are conducive to learning.

One or more embodiments may be utilized to ameliorate the problem of trainee attrition from physiological self-regulation training regimens by incorporating physiological self-regulation into geospatial scenario games and simulations, to thereby increase the motivation to learn health-enhancing physiological self-regulation skills. Physiologically modulated games and simulation scenarios add to the entertainment value of these activities by adding the challenge of requiring a player to master physiological self-regulation skills in addition to typical game mastery skills. Thus, controlling the physiological state, or learning to self-induce physiologic changes, is an additional skill requirement or challenge requiring a participant to self-regulate their own physiological signals in order to achieve a game or simulation goal.

In some embodiments, physiological self-regulation exercise challenges may take the place of or be combined with physical exercise tasks in a parcourse training scenario that may also involve orienteering in both physical and fantasy-adventure space. One or more embodiments may increase the entertainment value of orienteering-type games and simulations by adding the challenge of requiring a player to master physiological self-regulation skill in addition to orienteering skills. Controlling one's physiological state or learning to self-induce physiologic changes is an additional skill requirement or challenge added to the parcourse/orienteering-type games and simulations. The requirement for physiological self-regulation encourages the learning of health-enhancing physiological self-regulation skills and adds a unique challenge that enhances the participant's immersion in the game or simulation experience.

Turning now to the figures, FIG. 1 shows an example exercise course 20 that may be utilized in one or more embodiments of the present disclosure. The exercise course 20 may be part of a parcourse or the like. The course 20 may include one or more pieces of exercise equipment 24A-24D. In various implementations, the pieces of exercise equipment 24A-24D may be positioned relatively close to one another (e.g. several feet apart), or they may be spaced apart at different locations. In the example shown in FIG. 1, station 20 includes a stationary exercise bike 24A, a weight-lifting machine 24B, treadmill 24C, and pullup bars 24D. One or more of the exercise devices 24A-24D may be configured to communicate wirelessly with a smartphone 36A, 36B of users/participants 28A, 28B, respectively. Participants 28A, 28B, etc. may be prompted to accomplish a physiological self-regulation challenge as part of the course 20, and/or for each device 24A-24D. For example, the participants 28A, 28B may be required to accomplish one or more physiological self-regulation goals/challenges prior to engaging in a physical activity that utilizes one or more of the pieces of exercise equipment 24A-24D. Biofeedback devices such as headsets 32A, 32B may be worn by participants 28A-28B. The headsets 32A, 32B monitor physiological signals such as brain waves, heartrate, and body temperature. The headsets 32A, 32B may be configured to wirelessly communicate with mobile communication devices such as smartphones 36A, 36B, tablets, computers, wearable technology, or additional fitness tracking devices. It will be understood that virtually any suitable device may be utilized in connection with the present disclosure, and use of a headset and a smartphone are merely examples of suitable devices. The performance of physiological self-regulation may be monitored by various forms of wearable technology or fitness trackers, such as the headsets 32A, 32B. Headsets 32A, 32B may comprise a MUSE headband available from InteraXon, Inc. of Ontario Canada. The headsets 32A, 32B may derive signals representing psychophysiological functions from electroencephalographic (EEG) signals, and derives brain state values representing cognitive engagement.

The brainwave monitoring functionality can be used to encourage a brain state conducive to physical activity, learning or other task. As discussed in more detail below, one or more smartphones 36A, 36B may be configured (e.g. programmed) to process physiological data received from headsets 32A, 32B and/or other devices, and to display instructions and other information on the display screens of the smartphones 36A, 36B. Software (e.g. an "App") may be installed on smartphones 36A, 36B to thereby configure the smartphones 36A, 36B to provide data processing, user instructions, etc. to one or more participants/users traversing a parcourse or the like.

In some implementations, participants 28A, 28B may be required to achieve a physiological goal (i.e. meet the requirements of a challenge) prior to performing a series of exercises associated with each piece of equipment 24A-24D. If the user achieves the physiological goal associated with a piece of equipment (e.g. stationary bike 24A), the user is rewarded with, for example, information concerning the exercises to be performed on the stationary bike 24A. If the pieces of exercise equipment are spaced-apart, the information (reward) may include information concerning the location of the next piece of exercise equipment. The physiological goals associated with each piece of exercise equipment 24A-24D may be the same or different. Participants 28A, 28B may be required to perform specific exercises for each piece of equipment 24A-24D in order to successfully complete the game (parcourse). Thus, in this scenario, participants must "unlock" information concerning the exercises to be performed in order to know how to perform/complete the specific exercises for each piece of equipment 24A-24D. If the exercise equipment 24A-24D is configured to communicate with smartphones 36A, 36B, the exercise equipment may be configured to require receiving a signal from a smartphone 36A, 36B indicating that a user has successfully achieved a physiological goal before the equipment can be "unlocked" to permit operation.

The exercise equipment may also be configured to monitor the participant's exercise activity and communicate with smartphones 36A, 36B, etc. A user may be required to achieve a specific exercise goal at each piece of exercise equipment in order to receive information on smartphone 36A, 36B, etc. concerning, for example, the location of the next piece of exercise equipment 24A-24D, or information concerning the physiological goal associated with the next piece of exercise equipment 24A-24D. Thus, participants may be required to achieve both physiological goals and exercise goals for each piece of exercise equipment 24A-24D in order to advance and complete the course 20.

Additionally or alternatively, in some embodiments the smartphones 36A-36B, etc. may also be configured to utilize location as a requirement. For example, if the pieces of exercise equipment 24A-24D are spaced-apart at different predefined locations, the smartphones 36A, 36B, etc. may be configured (e.g., programmed) to utilize GPS coordinates and require that participants 28A, 28B etc. be at the correct predefined location for a specific piece of exercise equipment 24A-24D before the participant 28A, 28B, etc. is provided with information concerning the physiological goal and/or exercise goal associated with a specific piece of exercise equipment.

In some embodiments, the headsets 32A, 32B, etc. and/or other devices (heartrate monitor, etc.) may additionally or alternatively be configured to monitor a user's physiological state and provide feedback via smartphones 36A, 36B, etc. while a user is exercising at a piece of exercise equipment 24A-24D. Thus, physiological goals and exercise goals may be combined and a user may be required to meet both goals in order to receive a "reward" (e.g. information concerning the location of the next piece of exercise equipment, or rest period) in order to advance through the course 20. For example, a user may be required to achieve a specific distance on treadmill 24C within a time limit, while also achieving a predefined physiological goal related to a physiological state that is measured by headset 32A, 32B, etc. while the participant is running on the treadmill. As discussed in more detail below in connection with FIG. 7, if a participant 28A, 28B, etc. is unable to achieve a physiological (biofeedback) goal and/or a physical exercise goal associated with a specific piece of exercise equipment 24A-24D, the level of difficulty of the physiological and/or physical goals may be reduced.

Individual participants 28A, 28B, etc. may be tested/evaluated prior to participating in course 20, and the physiological and/or exercise goals, may be tailored to the individual capabilities of each participant 28A, 28B. In this way, the requirements for course 20 can be adjusted to provide specific requirements for each participant to focus on specific physiological and/or physical limitations/abilities that are to be improved for a specific participant 28A, 28B etc.

Still further, data collected during the course 20 can be utilized to determine an individual's physical and/or physiological strengths and weaknesses, and to adjust the physiological and/or physical requirements (goals) for a specific user based on the determined strengths and/or weaknesses. For instance, the goals for a specific participant 28A, 28B, etc. may be adjusted to be different during a subsequent use of course 20. For example, if data concerning a specific participant collected during the participant's use of course 20 indicates that specific physiological states are associated with increased exercise performance for specific types of exercise, the physiological goals may be adjusted for a specific participant to require a user to achieve a physiological goal in connection with a specific piece of exercise equipment 24A-24D to thereby train a participant to achieve a specific physiological state that optimizes physical performance for a specific type of exercise for a particular participant.

In some embodiments, course 20 may optionally include stations (not shown) for which participants are required to perform mental tasks (e.g. solve problems, learn, etc.) along with (or instead of) physical exercise. For example, smartphones 36A, 36B, etc. may be configured to require participants to learn about a particular topic and successfully answer questions about the topic or to solve a puzzle, when a participant is at a piece of exercise equipment 24A-24D (or at a predefined location between pieces of exercise equipment 24A-24D), before a physiological goal for the location is deemed to be completed.

In some implementations, participants 28A, 28B, etc. may be required to successfully achieve a physiological goal associated with each mental task while a user is at a specific predefined location (e.g. GPS coordinates) before the smartphone 36A, 36B will provide the participant with access to the mental task. Furthermore, the physiological state of the participant may be monitored while the participant is completing the mental task. This data may be compared to an additional (or alternative) physiological goal that must be achieved. This data may also be utilized to determine if particular physiological states are conducive to problem solving, learning, etc. for a particular participant, and the specific physiological goals associated with specific mental tasks for a specific participant may be adjusted for future use of course 20 by a specific participant 28A, 28B, etc.

Figure 2:
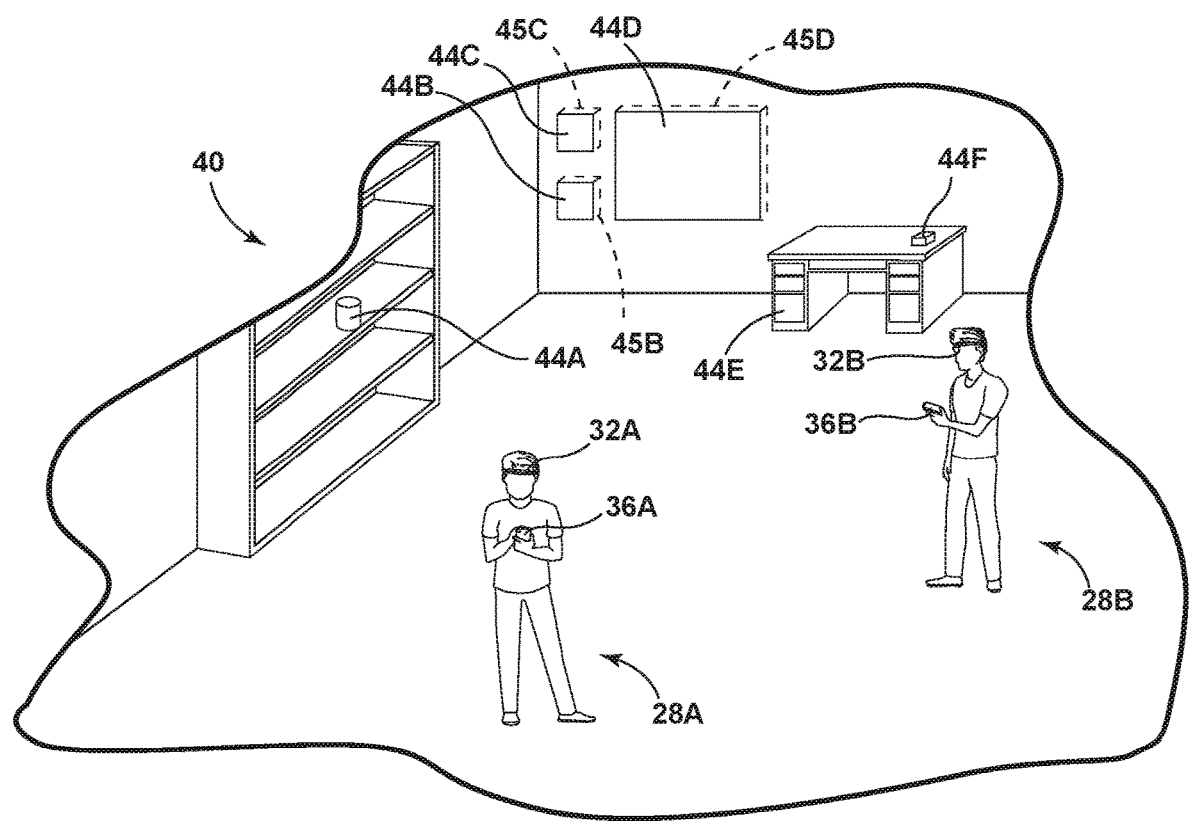
FIG. 2 is a partially schematic perspective view illustrating another aspect of the present disclosure.

Referring to FIG. 2, biofeedback to a user via a smartphone 36 or other device may also be utilized in an escape room problem solving game. Smartphones 36A, 36B of users 28A, 28B, respectively, may be configured (e.g., programmed) to receive physiological data from headsets 32A, 32B, respectively, and to provide instructions and/or other information to the participants 28A, 28B concerning the escape room game. In this example, escape room 40 includes one or more clues 44A-44F that participants 28A-28B must use in order to advance to the next stage of the problem-solving game or to escape the room 40 prior to the expiration of a time limit. Physiological self-regulation in combination with problem solving and/or strategy games creates an additional challenge that may be customizable to the individual participants 28A-28B. For example, a first participant 28A may have a first profile that is accessed from a smartphone 36 during the escape room problem solving game that has stored previous aptitudes for physiological self-regulation. A second user 28B may use a second smartphone 36B and headset 32B that has stored a second profile that is associated with a second user 28B. By referencing the stored previous aptitudes, the escape room problem solving game can present varying levels of difficulty based on the ability of a particular participant to meet physiological self-regulation challenges. The stored previous aptitudes may be stored, for example, in a program on the mobile communication device 36. These stored previous aptitudes may be accessed by various applications or software programs on the mobile communication device 36 as a reference point for different games and/or simulations with which the participant 28 wishes, or is required to be engaged. The performance of physiological self-regulation may be monitored by various forms of wearable technology or fitness trackers, such as the headset 32.

Users/participants 28A, 28B, etc. may be required to meet a predefined physiological goal associated with each location/clue 44A-44F before they are provided with a reward. The reward may comprise information provided by smartphones 36A, 36B, etc. (or other suitable device in escape room 40) that enables a user/participant 28A, 28B etc. to advance to the next clue/location 44A-44F. For example, one or more of clues/location 44B-44D may comprise an electronic display screen that provides a user/participant 28A, 28B etc. relevant information or hints if the physiological goal for a specific clue/location 44A-44F is achieved. Additionally or alternatively, the reward may provide participants additional tools, access, or other advantage in the locations. For instance, one or more of the clues/locations 44A-44F may comprise an item (e.g. a locked drawer 44E) that receives a wireless signal from a smartphone 36A, 36B etc. (or via a wireless network) to unlock the item (e.g. a drawer) to provide a user with physical access to the contents of the clue/location 44A-44F as a reward for meeting a predefined physiological goal. According to another example, one or more of clues/locations 44B-44D may comprise doors with electronic locks to selectively provide access to compartments 45B-45D, respectively, containing a key or other physical item that is required to advance to the next clue/location 44A-44F. As discussed in more detail below in connection with FIG. 7, in one or more embodiments, if a user/participant 28A, 28B etc. is initially unable to achieve a physiological goal (biofeedback exercise), the level of difficulty of the goal may be lowered.

Figure 3:
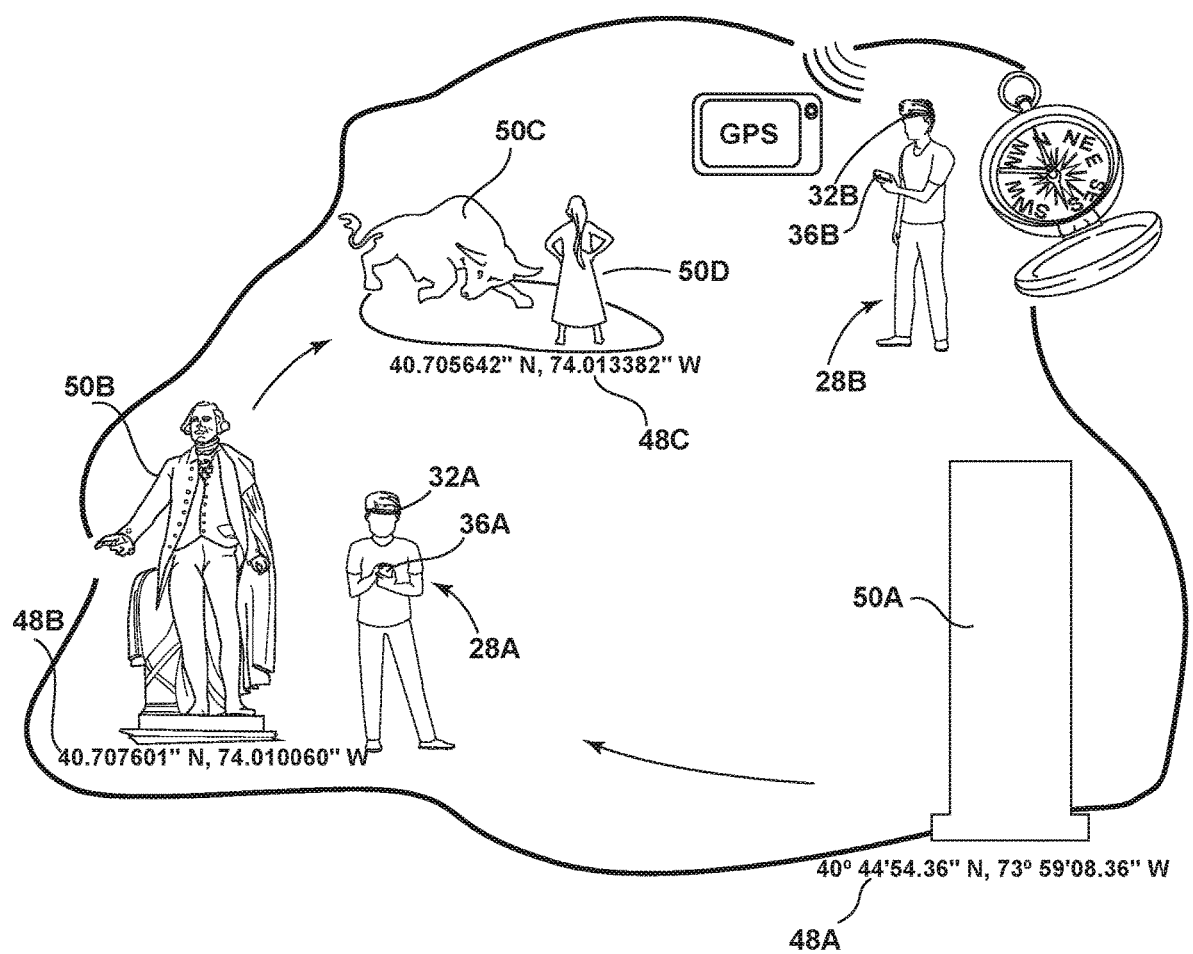
FIG. 3 is a partially schematic perspective view illustrating yet another aspect of the present disclosure.

With further reference to FIG. 3, one or more embodiments of the present disclosure utilize headsets 32A, 32B and one or more mobile communication devices 36A, 36B, respectively, to provide biofeedback in connection with orienteering (individual) or rogaining (team) games, such as geocaching. The participants 28A, 28B, etc. traverse physical geospatial locations 48A-48C at which are located items 50A-50D. The participants 28A, 28B, etc. may be operating under additional time constraints as they compete against other participants to traverse the course or reach locations prior to fellow participants. It will be understood that the locations 48A-48C, etc. may be located a significant distance from one another, such that the total course length may be significant (e.g. 10, 20, 30 or more miles). Also, although only three locations 48A-48C are shown in FIG. 3, the course may include four or more locations. Furthermore, although the locations of FIG. 3 are urban locations, it will be understood that the locations may comprise rural or wilderness locations/stations.

Smartphones 36A, 36B, etc. may be configured to process data from headsets 32A, 32B, etc., respectively, and to provide instructions and other information to the users 28A, 28B during the game. Examples of displays/communications are discussed in more detail below in connection with FIG. 8.

At each location 48A-48C, etc., the users/participants 28A, 28B, etc. may be required to achieve a physiological goal in order to receive information (or other reward). The information may comprise information about the item(s) 50A-50D at a location 48A-48C, and/or information that enables a user/participant 28A, 28B, etc. to find the next location 48A-48C. The smartphones 36A, 36B may be configured to determine/track the locations of each user/participant 28A, 28B, etc. (e.g. utilizing GPS), and the smartphones 36A, 36B etc. may be configured to require a user/participant 28A, 28B etc. to be at a specific predefined location 48A-48C, etc. at the time the predefined physiological goal is achieved in order to receive the information or other reward.

According to another aspect of the present disclosure (FIG. 4), one or more users/participants 28 tour a facility such as a museum 52 wearing a headset 32 to monitor physiological signals. The museum 52 includes stations 54A-54D having exhibits 60A-60D, respectively, and signs 56A-56D, respectively. The physiological states are communicated to a mobile communication device (e.g. smartphone 36) as the participants traverse the museum 52. The headset 32 and mobile communication device 36 may be configured to provide a self-guided tour. As the participants 28 reach the various stations 54A-54D, they may encounter signs 56A-56D, respectively that provide location information for navigation within an application ("App") provided on the smartphone 36. Signs 56A-56D may also provide information about the type of biofeedback/physiological self-regulation challenge (goal) that must be completed to unlock information about each station 54A-54D, respectively. If a participant achieves a physiological self-regulation challenge/goal for a particular station, the smartphone 36 provides the participant 28 with a reward such as information concerning the exhibit for that station. If a physiological goal is achieved, users/participants may be provided with other rewards such as tokens or points (stored on smartphones 36A, 36B, etc.) that can be used, for example, to purchase a souvenir upon completion of the tour. This type of a reward may be provided as an alternative to information, or in connection with information.

Figure 8:
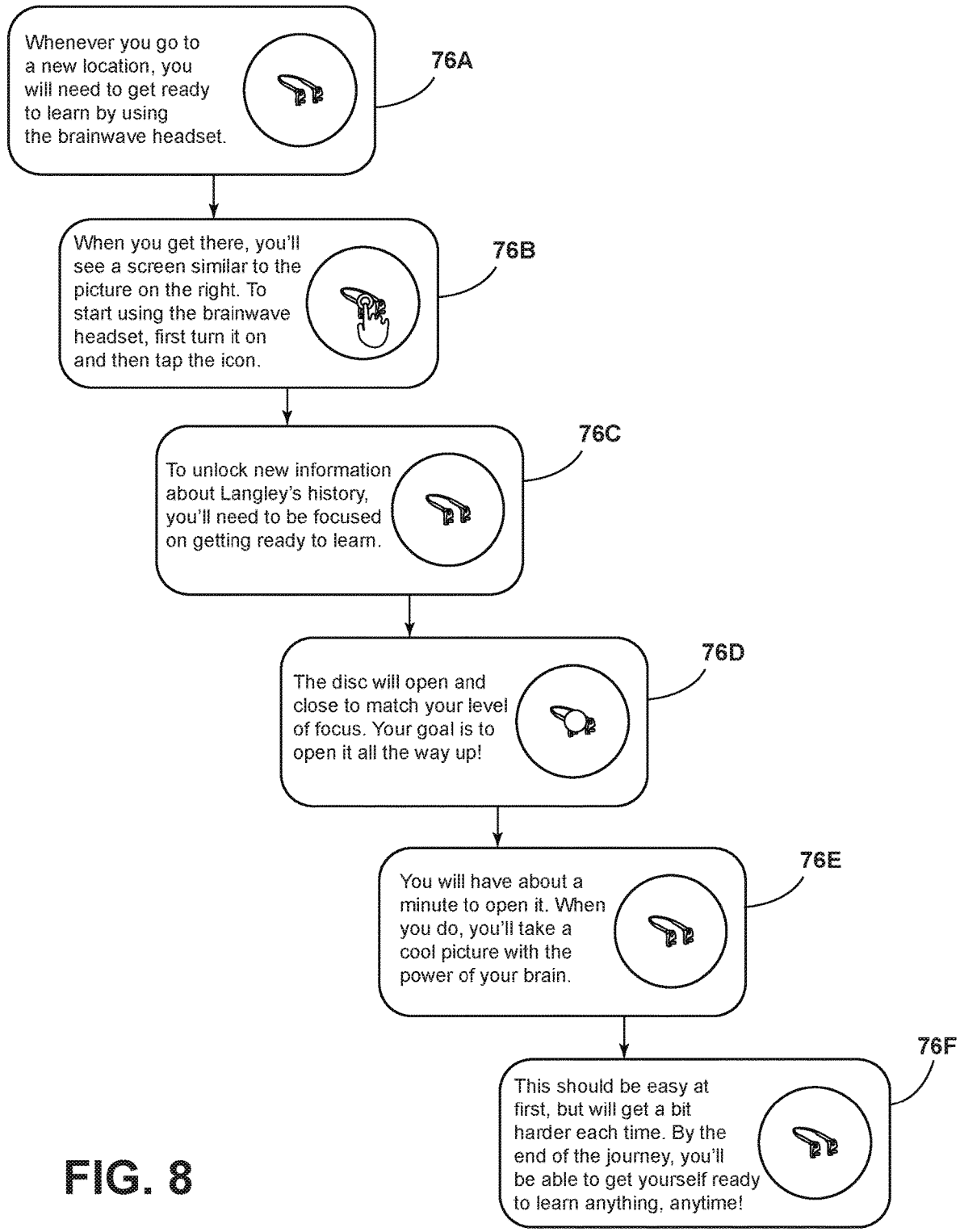
FIG. 8 is a schematic showing a series instructions displayed on an electronic device, wherein the instructions relate to use of a headband to provide feedback to a user concerning a physiological state of the user.

Example text and information that may be displayed on a smartphone 36 or other portable device in connection with a tour of museum 52 (FIG. 4), in one or more implementations, are shown in FIG. 8. Specifically, a message 76A "Whenever you go to a new location, you will need to get ready to learn by using the brainwave headset" may be displayed. A message 76B "When you get there, you'll see a screen similar to the picture on the right. To start using the brainwave headset, first turn it on and then tap the icon" may then be displayed. This may be followed by a message 76C "To unlock new information about Langley's history, you'll need to be focused on getting ready to learn," and a message 76D "The disc will open and close to match your level of focus. Your goal is to open it all the way up!" A message 76E "You will have about a minute to open it. When you do, you'll take a cool picture with the power of your brain" will then be displayed, followed by a message 76F "This should be easy at first but will get a bit harder each time. By the end of the journey, you'll be able to get yourself ready to learn anything, anytime!"

Figure 4:
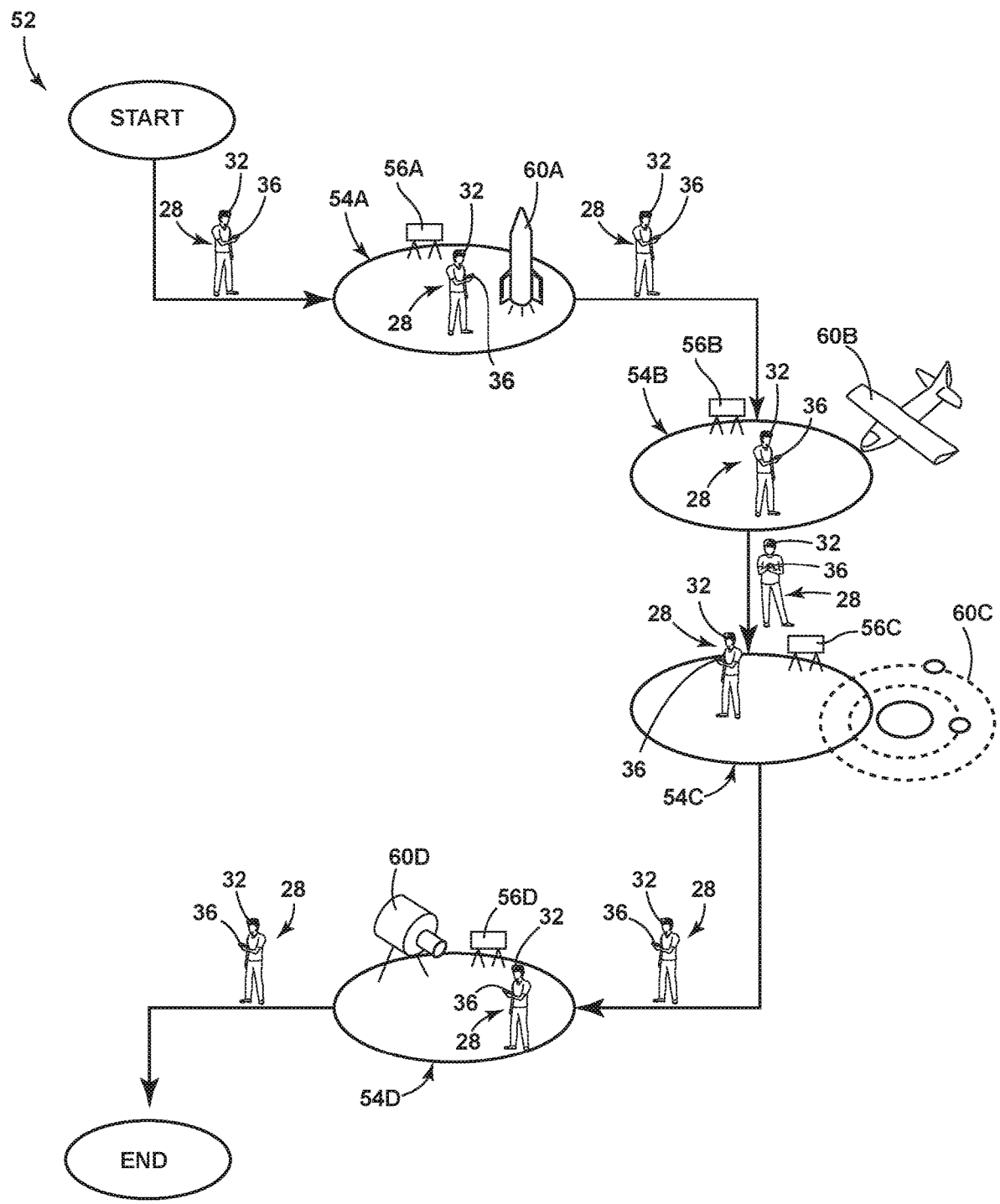
FIG. 4 is a partially schematic perspective view illustrating a further aspect of the present disclosure.

In some embodiments, the app utilized by smartphone 36 during the tour of FIG. 4 (or other activity) may be configured to provide a videogame that is played by the participants. The video game includes an in-game character that interacts with the participant 28 during the tour. As an example, the in-game character may be a character in another dimension and the participant 28 is challenged with assisting the character in achieving a game goal by producing a specified physiological signal having a target value, level, pattern, or timing characteristic. Simultaneous to or following the production of the specified physiological signal, the participant 28 navigates to various stations 54A-54D or various geospatial locations to progress through the in-game fictional story.

In some embodiments, the app may be configured to provide an augmented reality by depicting in-game character(s) and/or object(s) integrated with real-time video captured from a camera on the smartphone 36. Additionally or alternatively, an augmented reality may be provided by displaying in-game character(s) and/or object(s) via a transparent head-mounted display (e.g., eyeglass display). In some implementations, one or more in-game character(s) and/or object(s) may be displayed in response to the user satisfying a physiological goal defined for the location and/or activity. Additionally or alternatively, in some implementations, one or more displayed in-game character(s) and/or object(s) may provide physiological challenge(s) to the user. As an illustrative example, upon arriving in a designated location, the smartphone app may depict a magical animal in an augmented reality display. The user may be prompted to battle the magical animal using a weapon or character controlled at least in part by a particular physiological response. The magical animal may be defeated by the user when the requisite physiological response is exhibited by the user. In response to detecting the requisite physiological response, a reward may be provided to the user via the smartphone app (e.g., information, new in-game ability, new in-game mission, etc.).

In a further embodiment, where group-play is employed (e.g. FIG. 3), teams of participants 28 strive to best opposing teams in completing an adventure in an actual geospatial environment using navigational skills and the mobile communication device (e.g., smartphone 36) to navigate from location to location. As an illustrative example, the geospatial environment may comprise a wilderness area such as a National Park, an urban area, or other suitable environment. The environment may be configured to be similar to a parcourse in that a path or course is equipped with stations distributed along its length. Each participant 28 is required to exercise self-regulation of physiological signals monitored by their mobile communication device 36 via the headset 32, a heartrate monitor 64 (FIG. 5), or another physiological monitoring device, for example to achieve a game or simulation goal. Physiological self-regulation skill metrics may be based upon, for example, comparing physiological scores, standardizing scoring metrics based on an individual's baseline responses, a benchmark target or benchmark normative value.

As another illustrative example, some embodiments may be configured to provide biofeedback in connection with geospatial games such as golfing. Referring again to FIG. 3, for instance, headsets (e.g., 32A, 32B) and one or more mobile communication devices (e.g., 36A, 36B) may be utilized to provide biofeedback based on physiological responses of players during gameplay. As participants (e.g., 28A, 28B) traverse various physical geospatial locations on the course (e.g., tees, holes, sand traps, etc.), physiological responses exhibited by players may be measured and used to enhance gameplay (e.g., via one or more physiological challenges). For instance, smartphones 36A, 36B, etc. may be configured to process physiological data from headsets 32A, 32B, etc., respectively, and to provide instructions and other information to the users 28A, 28B during the game. Examples of displays/communications are discussed in more detail below in connection with FIG. 8. At each location 48A-48C, etc., the users/participants 28A, 28B, etc. may be required to achieve a physiological goal in order to receive a reward. The smartphones 36A, 36B may be configured to determine/track the locations of each user/participant 28A, 28B, etc. (e.g. utilizing GPS), and the smartphones 36A, 36B etc. may be configured to require a user/participant 28A, 28B etc. to complete a particular physiological goal at a specific predefined location before a particular reward is provided. In some implementations, the reward may comprise information about the golf hole(s) at a location such as pitch, distance to green, current wind speed, etc. Additionally or alternatively, reward may comprise an advantage to the player in the game. For example, such an advantage may include a do-over (i.e., mulligan) or choice to tee off from an amateur tee that is closer to the green. As another example, the advantage may include a disadvantage (e.g., restriction on the choice of club) that may be given out to one or more other players for one or more holes.

According to some aspects of the present disclosure, a participant 28 may be required to self-regulate their own physiological signals in order to achieve a game or simulation goal. Alternatively, a teammate may be required to self-regulate their physiological signals to achieve a game or simulation goal for the participant 28 (i.e., a participant's progress may depend upon a second participant's ability to self-regulate). In another alternative, an opponent participant 28 may be required to self-regulate their physiological signals to interfere with a game or simulation goal sought by the participant 28. It is contemplated that the game or simulation may include any of these variations individually or in combination.

Figure 5:
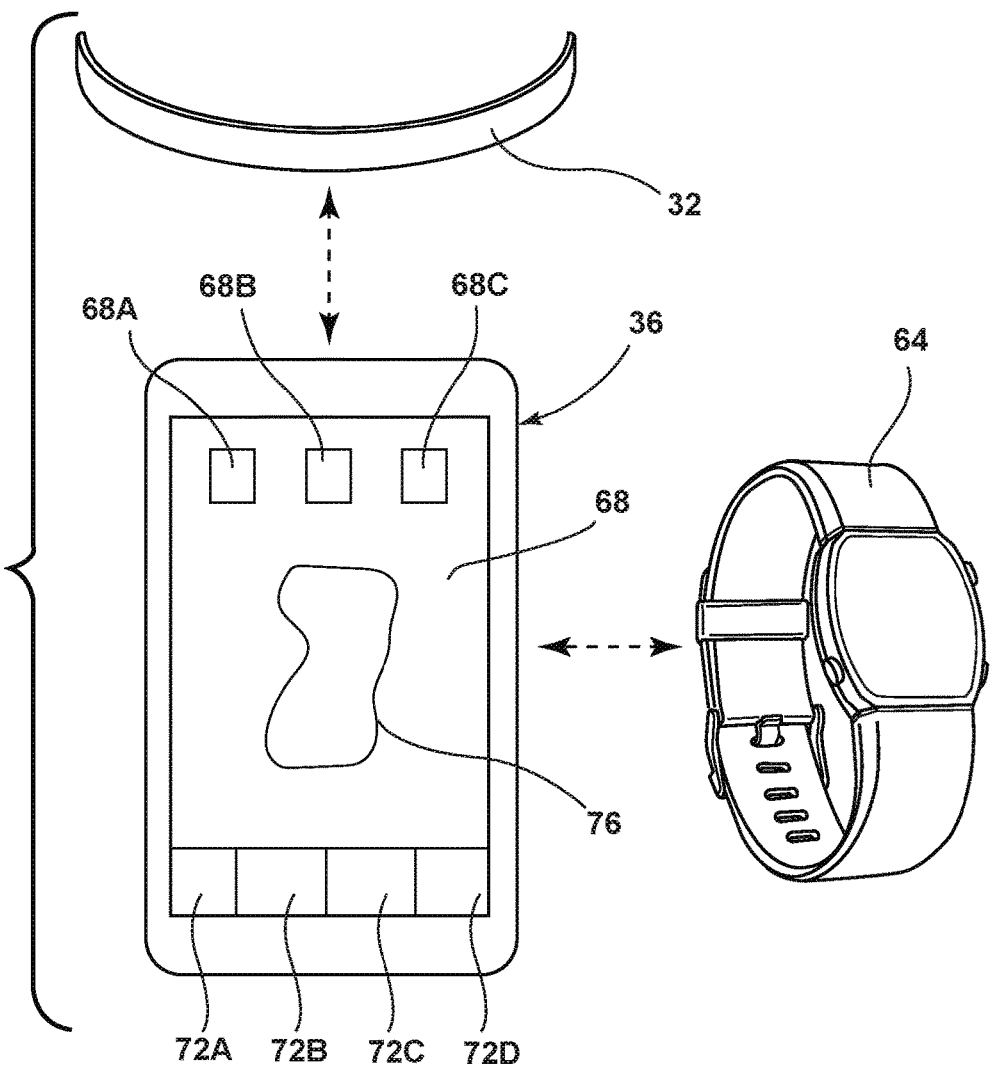
FIG. 5 is a partially schematic perspective view illustrating communication between an electronic device and one or more biofeedback devices.

Referring to FIG. 5, the mobile communication device 36 (see also FIG. 1) can communicate with the headset 32 as well as various other biofeedback technologies, such as a heartrate monitor 64. The communication between the mobile communication device 36 and the headset 32 or the heartrate monitor 64 can be either wired or wireless. The mobile communication device 36 can be configured (e.g., programmed) to provide various interactive displays 68A-68C on a touchscreen 68. Device 36 may also include user inputs such as buttons 72. Device 36 may be configured to provide a biofeedback display 76 that provides the participant 28 (FIG. 1) with feedback concerning their achievement of a physiological self-regulation goal. The information provided by the biofeedback display 76 may be utilized as a form of positive or negative feedback to the participant 28 regarding their achievement of a physiological self-regulation goal. For example, positive feedback provided by the biofeedback display 76 may include providing the participant 28 with health achievements (steps, calories, etc.), maps, comparative biofeedback to participants 28 within a network for a given course, historical content, riddles, puzzles, clues 44, and the like to reward achievement of the participant's 28 physiological self-regulation goal. Negative feedback provided by the biofeedback display 76 may include withholding from the participant 28 health achievements (steps, calories, etc.), maps, comparative biofeedback to participants 28 within a network for a given course, historical content, riddles, puzzles, clues 44, and the like to motivate striving for the participant's 28 physiological self-regulation goal.

Various embodiments of the present disclosure may employ integrated EEG signal and heartrate (cardio tachometer) signal monitoring. Further embodiments may employ brainwave signal monitoring, specifically an "engagement index" derived from brainwave signals. The engagement index has been defined previously (see Pope, A. T., Bogart, E. H., and Bartolome, D. S. (1995). Biocybernetic System Validates Index of Operator Engagement in Automated Task. Biological Psychology, 40, 187-195.) Other physiological signals that may be used include, but are not limited to, skin conductance signals, skin temperature signals, and respiration signals.

A noise-reducing enhancement may be desired for obtaining the electrical signal associated with monitoring heartrate. The heartrate signal may be derived, for example, using a photoplethysmograph sensor or electrocardiogram electrodes. One convenient method for obtaining the electrocardiogram heart signal is the use of chest band electrodes (not shown) in combination with a wireless transmitter (e.g., Polar Model T31 from Polar Electro USA). This technology minimizes movement artifact (electrical noise) and enables the present disclosure to be used conveniently with various mobile communication devices. An additional method for obtaining heartrate data from a participant 28 includes utilizing image analysis capabilities to sense slight changes in skin color (blushing) or temperature which occurs with each heartbeat. Monitoring heartrate with image analysis capabilities allows for unobtrusive (i.e., no sensors attached to subject) monitoring of the heartrate of a participant 28.

One or more embodiments of the present disclosure may additionally or alternatively employ facial expression recognition as a technology for inferring the physiological state of a participant 28. Facial expression recognition embodiments exploit the capability of a more advanced form of image analysis that interprets and/or resolves facial expression. Cameras (not shown) may be positioned at one or more locations of a course/path (e.g. FIGS. 1-4), and the cameras may be configured to communicate images of a user's face to a user's smartphone 36. The camera of the smartphone 36 may also be utilized to generate facial images that are processed by smartphone 36. In other embodiments, modulation between the functioning of gesture recognition and body movement recognition technologies may be utilized to derive the physiological state of the participant 28 based upon characteristics of physiological and/or body movement signals acquired by image acquisition and image analysis hardware/software.

Figure 6:
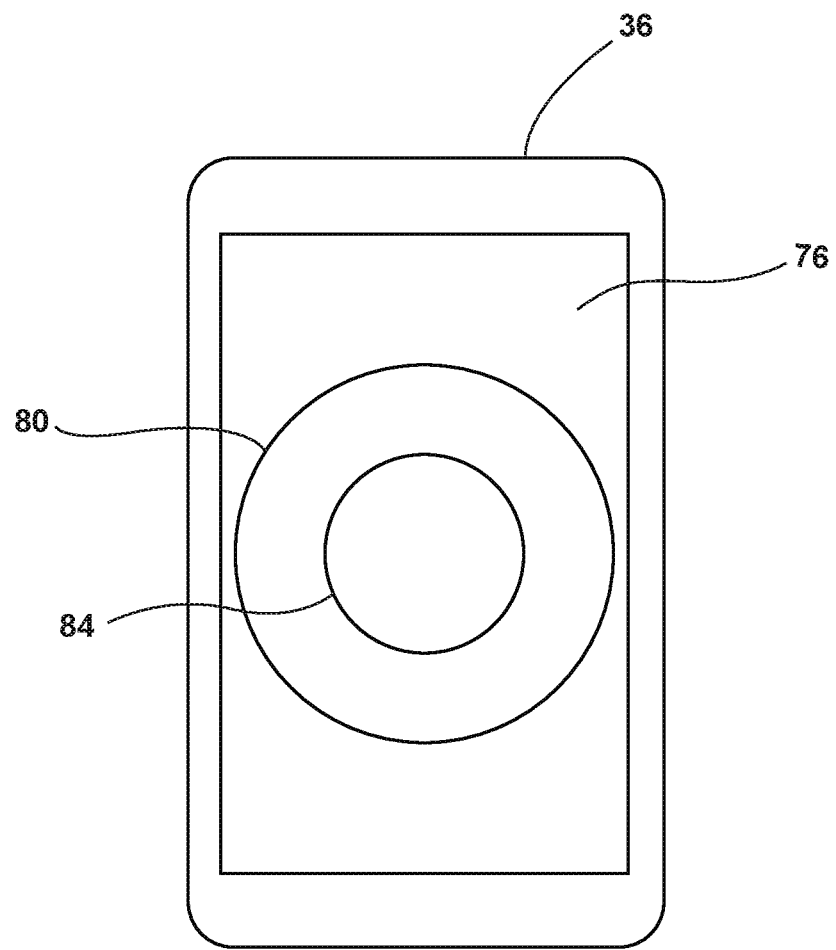
FIG. 6 is a partially schematic view of an electronic device having a display careen with an image that provides feedback to a participant regarding a physiological state of the user.

With reference to FIG. 6, mobile communication device 36 may be configured to interact with a headset 32 to provide a biofeedback display 76 that can be used in connection with an activity such as a tour of a facility (e.g. FIG. 4) following a sequence of instructions (e.g. FIG. 8). In the depicted example, a first ring 80 represents a physiological self-regulation goal. An inner second ring 84 represents the progress of the participant 28 (FIG. 1) toward the physiological self-regulation goal. A diameter of the second ring 84 may expand as a user comes closer to reaching a physiological self-regulation goal, and contract if a user's state becomes further from a physiological self-regulation goal. Once the diameter of the second ring 84 reaches the diameter of the first ring 80, a "portal" may open on the mobile communication device 36, taking a picture of an item at the current location and also revealing information and artifacts about a particular historical event, activity, or person associated with the current geospatial location in the facility course. The information may be presented in the form of text, photographs, videos, or other media. In some embodiments, the display of FIG. 6 may be utilized in connection with any of the tours/games/activities of FIGS. 1-5 and 7-9 to provide biofeedback to users/participants.

According to one example, the portal may enable communication with an in-app character 90 (FIG. 9) "living" in the future (e.g., 100 years in the future) once the portal has been opened by meeting the physiological self-regulation goal. As the participant 28 traverses the course, the onscreen character 90 may be presented as a child from 100 years in the future who's interested in learning the subject matter the participant 28 is currently learning (e.g., history about a building celebrating a centennial) in preparation for a visit to the same building as the building celebrates a bicentennial commemoration. The onscreen character 90 may possess a "fashion accessory" that is, for example, an advanced brainwave headset that connects with the participant's 28 headset 32 (FIG. 1).

Figure 9:
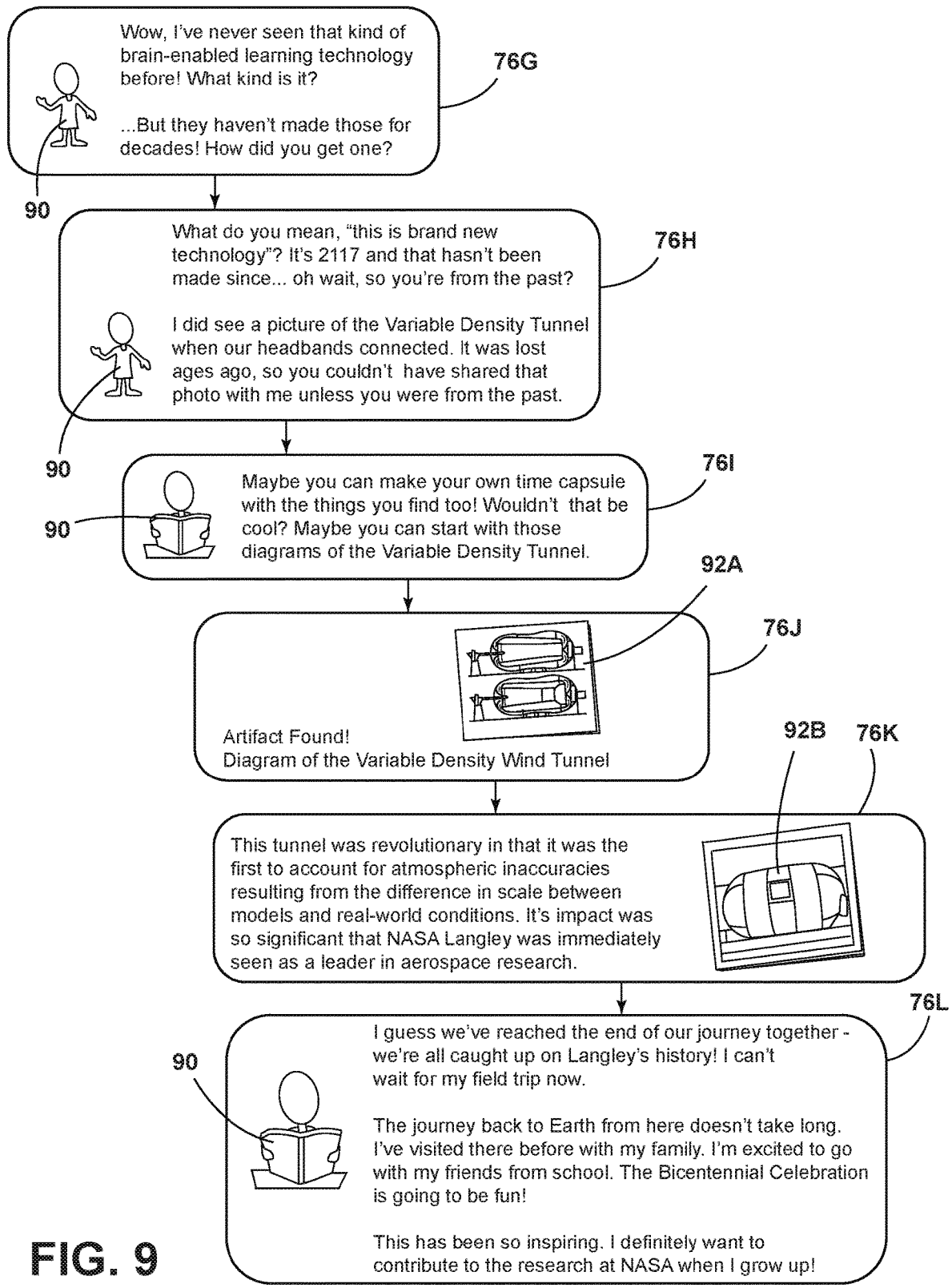
FIG. 9 is a schematic showing a series of messages from an on-screen character that are displayed on an electronic device.

The onscreen character 90 may engage with the participant 28 in the form of questions, comments, reminders to pick up artifacts, etc. as shown by the displays 76G-76L. More specifically, display 76G may comprise a message "Wow, I've never seen that kind of brain-enabled learning technology before! What kind is it? . . . But they haven't made those for decades! How did you get one?" Display 76H may comprise a message "What do you mean, 'this is brand new technology'? It's a 2117 and that hasn't been made since . . . oh wait, so you're from the past?" Message 76I may state "Maybe you can make your own time capsule with the things you find too! Wouldn't that be cool? Maybe you can start with those diagrams of the variable density tunnel." Display 76J may include the message "Artifact Found! Diagrams for the variable density wind tunnel" and schematic images 92A of a wind tunnel. Display 76K may comprise a message "This tunnel was revolutionary in that it was the first to account for atmospheric inaccuracies resulting from the difference in scale between models and real-world conditions. Its impact was so significant that NASA Langley was immediately seen as a leader in aerospace research," and a photographic image 92B of a wind tunnel. The display 76L may comprise a message "I guess we've reached the end of our journey together—we're all caught up on Langley's history! I can't wait for my field trip now. The journey back to Earth from here doesn't take long, I've visited there before with my family. I'm excited to go with my friends from school. The Bicentennial Celebration is going to be fun! This has been so inspiring. I definitely want to contribute to the research at NASA when I grow up!" It will be understood that the displays 76G-76L of FIG. 9 are merely an example of an implementation of the present disclosure.

The onscreen character 90 may become increasingly helpful to or interactive with the participant 28 as the participant 28 traverses the course (e.g., provide more information, more detailed information, hints, etc.). The onscreen character/traveling companion 90 may not appear to the participant 28 at first, rather the onscreen character 90 may only text the participant 28 onscreen. Next, the onscreen character 90 may appear as a 2-dimensional (2D) black and white character (not shown) while texting with the participant 28. Then the onscreen character 90 may appear as a 2D color character and communicate verbally through audio capabilities of the mobile communication device 36. The onscreen character 90 may then appear as a hologram in full color (not shown) and continue to communicate verbally. The onscreen character 90 may eventually be revealed to be a Mars colonist child. The mobile communication device 36 display (FIG. 6) may alternate between the onscreen character 90 and the biofeedback display 76 as the user/participant 28 traverses the course (FIG. 4), and the onscreen character 90 may voice encouraging messages while the user/participant is trying to achieve the physiological goal with the biofeedback display. The course (FIG. 4) may be provided with a 3-D printer (not shown) near the end of the course. As the participant 28 nears the end of the course, the onscreen character 90 may instruct the participant 28 to send 3-D printed models of the participant's artifact selections to a time capsule and miniature versions of the participant's artifact selections to a 3D printer referred to by the character as "a primitive additive manufacturing device." A virtual in-game time capsule can subsequently be created and shared via a social media application installed on the mobile communication device 36. Accordingly, participants 28 may publish their artifact selections for other participants to view.

Users/participants may be required to achieve a physiological goal while the user/participant is at a predefined location in order to cause onscreen character 90 to provide information, in order to earn points that can be used to print an object using the 3D printer, and/or receive another reward.

A method 100 (FIG. 7) may be utilized to implement the activities of FIGS. 1-4 and/or other activities/games. Method 100 may begin with a step 104 which includes starting an application 68. Application 68 may be started by, for example, touching an interactive display 68A, 68B, etc. (FIG. 5) of a touch screen of a smartphone 36. Application 68 typically comprises software that has been installed on a smartphone 36 or other suitable device. During start 104 (or later in process 100), the application 68 of device 36 may prompt the participant to enter information concerning the participant, and the application 68 may then determine an initial physiological goal based on the user's inputs. Examples of physiological goals to be achieved include a predefined level of an engagement index (e.g. Pope, et al. 1995), a predefined heart rate, and a predefined respiration rate and/or a predefined difference of these physiological measures relative to measured baselines of a participant. The application 68 may suggest one or more goals, and prompt the applicant to select a goal. Also, the application 68 may display instructions and/or other information concerning the course, the stations/challenges that will be encountered along the course, etc. Once the application 68 has been started, the mobile communication device 36 is paired with a device (e.g. headset 32) for measuring a user's physiological state at step 108. Once the headset 32 has been paired to the mobile communication device 36, the headset 32 begins monitoring the physiological state of a user/participant at step 112. Headset 32 may continuously or periodically transmit data concerning the physiological state to device 36.

Method 100 then advances to step 116 and the participant 28 is prompted to go to the next station of the course. The participant 28 arrives at the next station at step 120. Once the participant arrives at the next station, the participant engages in a biofeedback exercise or challenge at step 124. The biofeedback exercise may begin with a baselining period during which the participant's engagement index or heart rate or respiration rate or other physiological parameter is monitored and a baseline measure of the parameter is calculated. This measure or some fraction or multiple of it may be substituted for the previous physiological goal for the participant. In some embodiments, the determination of physiological goals to be used for each location may be based in-part on the determined baseline for the user. Additionally or alternatively, the determination of the physiological goals may be based upon, for example, comparison with physiological measure of others, a benchmark target or benchmark normative value.

At step 128 the participant 28 is provided feedback regarding the physiological goal. Step 132 determines whether or not the participant 28 achieved the physiological goal. If the physiological goal was not achieved by the participant 28, then method 100 advances to step 144 where the application determines if fewer than a pre-determined number of attempts, II, have been made. If fewer than n number of attempts has been made to accomplish the biofeedback exercise, then the participant 28 is provided another opportunity to complete the biofeedback exercise at the same difficulty level at step 124. However, if greater than n number of attempts has been made to accomplish the biofeedback exercise at step 144, method 100 advances to step 148, and the level of difficulty of completing the biofeedback exercise is lowered to increase the likelihood that the participant 28 completes the biofeedback exercise. After lowering the level of difficulty at step 148, method 100 returns to step 124. If the physiological goal was achieved by the participant 28 at step 132, the method 100 advances to step 134, and the participant is provided access to engage in an activity/exercise.

Figure 7:
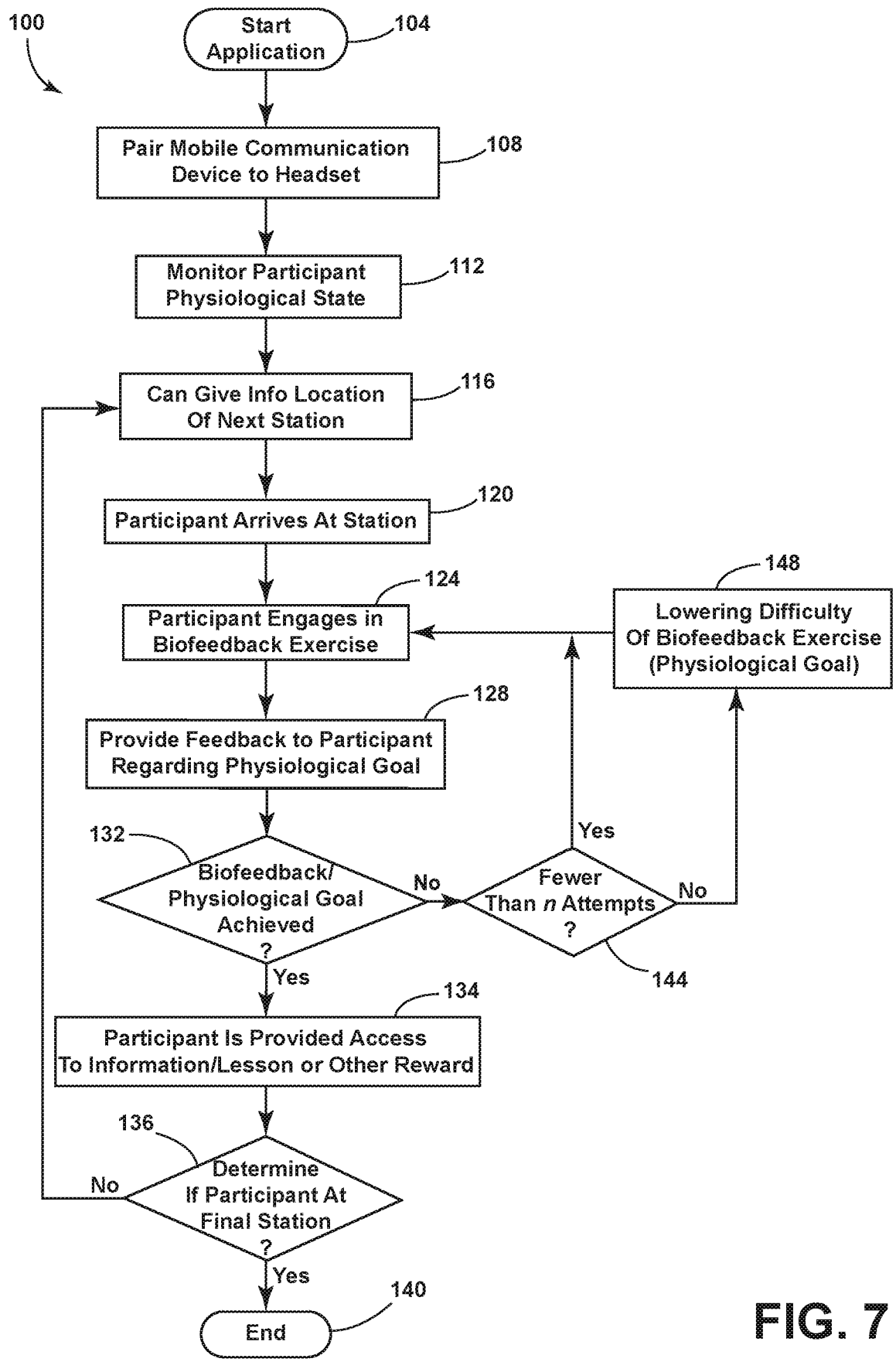
FIG. 7 is a flowchart illustrating a method of incorporating a physiological self-regulation challenge into a series of activities/tasks/exercises.

The exercise/task may comprise a physical activity (e.g. stations 24A-24D; FIG. 1), or a "clue" activity 44A-44F (FIG. 2) if the course comprises an escape room activity. The activity/exercise of step 134 may, alternatively, viewing an item 50A-50D (FIG. 3) at locations 48A-48C. Alternatively, if the course comprises a tour of a museum or similar facility, the activity/exercise may comprise viewing an item 56A-56C at a course 54A-54D (FIG. 4). Still further, the stations of steps 116 and 120 may comprise locations in an actual geospatial environment of an adventure in, for example, a wilderness area. At step 136 of method 100, the application 68 determines whether or not the participant 28 has reached the final station in the course. If the participant 28 has reached the final course 20, the method 100 is terminated at step 140. If the participant 28 has not reached the final course 20, then the method 100 returns to step 116 and progresses through the method 100 as shown in FIG. 7 until the participant 28 completes the course.

The components utilized in the present disclosure include, but are not limited to, the mobile communication device 36 (e.g., smartphone, tablet, computer, etc.), a physiological signal processing routine for the mobile communication device 36 (e.g., heartrate monitor, electroencephalographic (EEG) signal acquisition technology, etc.), a biofeedback display 76 and/or implicit brain-computer interface, global positioning system (GPS) functionality for the mobile communication device 36, mobile computing capabilities, for example, within the mobile communication device 36 that integrate the above components into an orienteering-type/adventure fantasy game or simulation Methods that incorporate the concepts disclosed herein may include the following steps in any order and with steps added or removed from the sequence:
monitoring a physiological signal or signals from a participant 28;
monitoring a geospatial location of a participant 28 as the participant 28 traverses a course;
arriving at a particular geospatial location or station;
presenting participant 28 with a physiological self-regulation challenge; and
monitoring the participant's 28 physiological state with the physiological processing routine on the mobile communication device 36.

The physiological self-regulation challenge may include one or more of the following tasks:
producing a specified physiological signal having a target value, level, pattern and/or timing characteristics;
constructing a physiological monitoring device, such as the headset 32, using modular components and instruction from an in-game character;
utilizing the constructed physiological monitoring device to produce a specified physiological signal having a target value, level, pattern or timing characteristics;
producing or meeting the specified physiological signal/goal target characteristics; and
unlocking content/information on the mobile communication device 36.

The content/information that is unlocked by meeting the specified physiological goal/target characteristics may be content related to a particular subject, information about the next geospatial location to visit, and/or other sought after information. The participant 28 may continue to traverse the physiological self-regulation course until an overall objective is met, which may be the accumulation of a score, arrival at the course end, or other goal.

An exemplary embodiment of the present disclosure would function as follows:
a participant 28 traverses a prescribed course within a building (e.g., museum) to learn about the history of the building, an organization, or subject matter that is of interest to visitors of the building;
the mobile communication device 36 monitors the participant's 28 geospatial location;
the participant's 28 brainwave activity is monitored and communicated to the mobile communication device 36 using a headset 32 equipped with EEG signal acquisition technology;
upon arrival at a prescribed geospatial location of the course that is associated with a particular historical event, activity, or person, the participant 28 is presented with a physiological self-regulation challenge, for example, producing brain state values representing cognitive engagement;
the brain state values are registered by the headset 32 and communicated to the mobile communication device 36;
as the participant 28 endeavors to produce a target brain state, the biofeedback display 76 provides a measure of progress toward the target brain state to the participant 28 (e.g., diameter of an annular ring on the mobile communication device 36 fluctuates with the progress toward and/or away from the target brain state);
once the target brain state has been met, the biofeedback display 76 allows access to the information available at the given location;
as the participant 28 advances through the course, the information provided via the biofeedback display 76 becomes more detailed, more interactive, and/or more engaging;
the participant 28 continues traversing the course continues to perform the self-regulation exercises to receive information that is educational;
while traversing the course, the participant 28 may collect "artifacts" along the way that pertain to historical events, activities, and/or persons associated with the each geospatial location (e.g., in the form of text, photographs, videos, or other media); and
at the end of the course the participant 28 may choose to place a number of the collected artifacts in both an in-game virtual time capsule and a real-time physical time capsule.

In addition to enhancing entertainment value by making orienteering-type games and simulations more challenging, physiological self-regulation practice and performance also has advantages for encouraging health-enhancing physiological self-regulation skills. Physiological self-regulation is also beneficial for therapeutic amplification of healthful physiological characteristics. The present disclosure blends physiological self-regulation into popular geocaching and/or orienteering-type games and simulations in such a way that the entertainment value of the games is enhanced. Additionally, the physiological self-regulation exercises offer benefits to the participant 28 in other contexts. For example, if the challenge involves the self-regulation of a mental state associated with being prepared to learn new information, then a participant 28 who becomes proficient at the self-regulation challenges would be better able to prepare themselves to take in new information in other settings (e.g., classroom, on-the-job, etc.).

The present disclosure requires participants 28 to self-regulate physiological signals to overcome challenges presented in games and/or simulations. Acquisition of self-regulation skill by the participant 28 requires that the participant 28 undergo physiological self-regulation training (mastery of anxiety and/or inattention states).

In order to perform the self-regulation training, the participant may be required to construct one or more items such as the hardware and/or software necessary to complete the training, to thereby provide a constructionism educational experience. The cycle of construct, train, and perform may repeat throughout the game or simulation experience, for example, employing various physiological modalities and their corresponding instrumentation construction requirements. Construction of software components or programs within the tasks of the games or simulations may be accomplished, for example, with various known software development kits.

With respect to constructing the hardware, the participant 28 may be provided with several pieces of a physiological monitoring device and instructions from the onscreen character displayed by device 36 for assembling the physiological monitoring device. The constructed physiological monitoring device can then connect with the mobile communication device 36 in a wired or wireless fashion to enable the participant 28 to complete a physiological self-regulation challenge.

It has been suggested that constructivist learning happens especially well when people are engaged in constructing an item that is external to themselves (e.g. a sand castle, a machine, a computer program or a book). Such constructionism educational experiences are effective in fostering engagement in the learning process. Important aspects of learning (comprehension and retention) are facilitated by certain states of physiological arousal (e.g., excitement, challenge) and hindered by others (e.g., anxiety, inattention, boredom). While constructionism educational experiences provide the components of excitement and challenge, physiological self-regulation training supports learning through participant 28 mastery of anxiety and/or inattention states. The present disclosure integrates these experiences within the context of gameplay.

It is to be understood that variations and modifications can be made on the aforementioned structure without departing from the concepts of the present invention, and further it is to be understood that such concepts are intended to be covered by the following claims unless these claims by their language expressly state otherwise.

What is claimed is:

1. A method of improving physiological self-regulation skills of a participant, the method comprising:
providing a series of physiological self-regulation challenges for the participant, with each of the physiological self-regulation challenges separate but related to a respective one of a series of predefined activities for the participant, with the predefined activities each at a respective predefined spaced-apart location and related to a respective one of the physiological self-regulation skills;
determining respective physiological self-regulation goals for the self-regulation challenges, wherein the physiological self-regulation goals comprise achieving by self-regulation a respective target brain state conducive to learning or problem solving, and wherein the target brain states are selected for enhanced performing of the respective predefined activities;
determining a location of the participant; and
determining the location of the participant is one of the predefined spaced apart locations,
determining the predefined activity corresponding to the predefined location and determining the respective self-regulation challenge for the determined one of the predefined activities;
utilizing a sensing device to measure a physiological brain state of the participant while the participant is at the predefined location prior to the participant participating in the predefined activity, wherein the sensing device is configured to measure brain state values representing cognitive engagement;
comparing the measured physiological brain state of the participant to the target brain state of the self-regulation physiological goal for the determined self-regulation challenge;
causing a mobile communication device to communicate to the participant whether or not the participant has achieved the physiological self-regulation goal for the determined self-regulation challenge; and
based upon a determination that the participant achieves the physiological self-regulation goal, providing the participant with a predefined reward that includes required information or required access for performing the predefined activity at the predefined location, location information for a next one of the predefined locations, or both,
wherein the participant benefits from improvement in the physiological self-regulation skills and improvement in the ability to complete the predefined activities as the participant advances through the physiological self-regulation challenges and the predefined activities at the predefined spaced-apart locations.

2. The method of claim 1, wherein:
the reward further comprises actuation of a device at the predefined location.

3. The method of claim 1, including:
adjusting the physiological goal for the self-regulation challenge if the participant does not achieve the physiological goal for the challenge.

4. The method of claim 3, wherein:
adjusting the physiological goal for the challenge includes reducing a level of difficulty of the physiological goal.

5. The method of claim 4, wherein:
the level of difficulty of the physiological goal is only reduced if the participant has attempted to achieve the physiological goal for the challenge at least a predefined number of times.

6. The method of claim 3, including:
prompting the participant to repeat the challenge if the participant does not achieve the physiological goal for the challenge.

7. The method of claim 5, including:
causing the mobile communication device to display information indicating how close the participant is to the physiological goal for the challenge and that the participant did or did not achieve the physiological goal.

8. The method of claim 1, wherein:
the predefined reward comprises educational material.

9. The method of claim 1, wherein:
the participant comprises one member of a group of participants, wherein a plurality of groups of participants are required to navigate to a plurality of the predefined locations, wherein the plurality of the predefined locations are spaced-apart along a course.

10. The method of claim 1, wherein:
the sensing device further comprises at least one of an electroencephalography (EEG) device and a heart rate monitor; and
wherein the physiological goal further comprises at least one of an EEG signal in which a predefined engagement index is above a predefined level, a heart rate below a predefined rate and a predefined difference of these physiological measures from a participant's baseline measures of them.

11. The method of claim 1, wherein:
the sensing device further comprises a facial recognition device that resolves facial expressions of a participant; and
wherein at least one of the physiological goals further comprises a facial expression in which facial features indicate cognitive engagement.

12. The method of claim 1, wherein:
the predefined activities further comprise physical activities and viewing items disposed at each predefined location.

13. The method of claim 2, wherein:
the device further comprises a powered lock and the reward includes unlocking the lock to allow the participant access to a space containing a clue of an escape room game.

14. A method of improving physiological self-regulation skills of a participant, the method comprising:
providing a series of predefined mental activities for the participant at respective predefined spaced-apart locations;
providing a series of physiological self-regulation challenges for the participant with each of the physiological self-regulation challenges separate but related to a respective one of the predefined mental activities at the respective predefined spaced-apart locations and related to a respective one of the physiological self-regulation skills;
providing the participant with information concerning the predefined locations and mental activities;
determining respective physiological self-regulation goals for the physiological self-regulation challenges at the predefined locations, wherein the physiological self-regulation goals comprise achieving by self-regulation a target brain state conducive to learning or problem solving;
utilizing a sensing device to measure a physiological brain state of the participant when the participant is at each predefined location prior to the participant participating in the predefined mental activity, wherein the sensing device is a wearable technology device configured to measure brain state values representing cognitive engagement;
comparing the measured physiological brain state of the participant to the target brain state of the physiological goal for the determined self-regulation challenge;
providing feedback to the participant concerning the participant's measured physiological brain state when the participant is at each predefined location;
providing the participant with a predefined reward if the participant achieves the determined physiological self-regulation goal for the predefined location the participant is at, wherein the predefined reward includes educational material,
wherein the participant benefits from improvement in the physiological self-regulation skills and improvement in the ability to complete the predefined mental activities as the participant advances through the physiological self-regulation challenges and the predefined mental activities at the predefined spaced-apart locations.

15. The method of claim 14, including:
utilizing a display screen of a portable communication device to provide feedback to the participant concerning the participant's physiological state.

16. A method of improving physiological self-regulation skills of a participant, the method comprising:
providing a series of physiological self-regulation challenges for the participant, with each of the physiological self-regulation challenges separate but related to a respective one of a series of predefined activities at respective predefined spaced-apart locations and related to a respective one of the physiological self-regulation skills;
determining respective physiological self-regulation goals for the self-regulation challenges, wherein the physiological self-regulation goals include achieving by self-regulation a target brain state conducive to learning or problem solving, and wherein the target brain states are selected for enhanced performing of the respective predefined activities;
determining a location of the participant; and
determining the location of the participant is one of the predefined spaced apart locations,
determining the predefined activity corresponding to the determined location and determining the respective self-regulation challenge for the determined one of the predefined activities;
utilizing a sensing device to measure a physiological brain state of the participant while the participant is at the predefined location, wherein the sensing device is configured to measure brain state values representing cognitive engagement;
comparing the measured physiological brain state of the participant to the target brain state of the physiological goal for the determined self-regulation challenge;
causing a mobile communication device to communicate to the participant whether or not the participant has achieved the physiological self-regulation goal for the determined self-regulation challenge; and
based upon a determination that the participant achieves the physiological self-regulation goal, providing the participant with a predefined reward that includes required information or required access for performing the predefined activity at the predefined location, location information for a next one of the predefined locations, or a combination thereof, wherein the participant benefits from improved physiological self-regulation skills as the participant advances through the predefined activities at the predefined spaced-apart locations.

* * * * *